United States Patent [19]

Ehrlich et al.

[11] 4,097,691

[45] Jun. 27, 1978

[54] REMOTE TELEPHONE COUPLER AS FOR MEDICAL EMERGENCY DATA TRANSMISSION

[75] Inventors: Stephen Jeffrey Ehrlich, Sunrise; Edward Robert Beyer, Pompano Beach, both of Fla.

[73] Assignee: Motorola, Inc., Schaumburg, Ill.

[21] Appl. No.: 812,927

[22] Filed: Jul. 5, 1977

[51] Int. Cl.² ............................................. H04M 11/00
[52] U.S. Cl. ..................................................... 179/2 C
[58] Field of Search ..................... 179/2 C, 1 C, 2 DP

[56] References Cited

U.S. PATENT DOCUMENTS

| 3,541,261 | 11/1970 | Okleshen et al. | 179/1 C |
|---|---|---|---|
| 3,992,583 | 11/1976 | Davis et al. | 179/2 C |

Primary Examiner—Kathleen H. Claffy
Assistant Examiner—Kenneth A. Chayt
Attorney, Agent, or Firm—Margaret Marsh Parker; James W. Gillman

[57] ABSTRACT

An acoustic telephone coupler for use in transmitting medical data over telephone lines and adapts to accommodate any telephone handset configuration. The slim coupler base further functions as a spool for a lengthy cable, and a dual purpose strap alternatively retains the cable and cable connector on the spool or a telephone handset against the transducers of the coupler.

6 Claims, 7 Drawing Figures

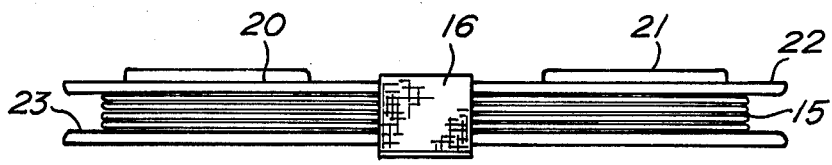
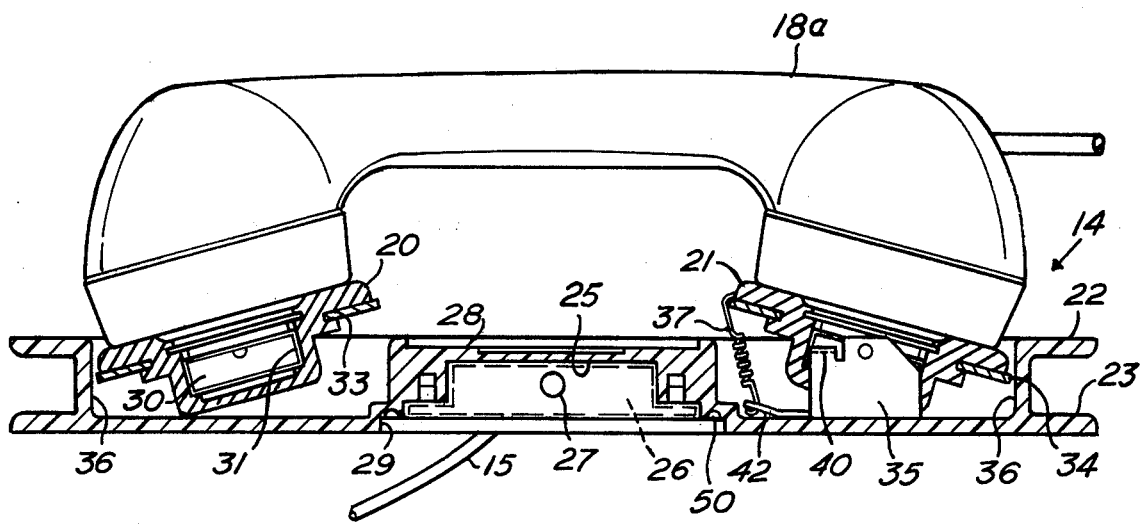
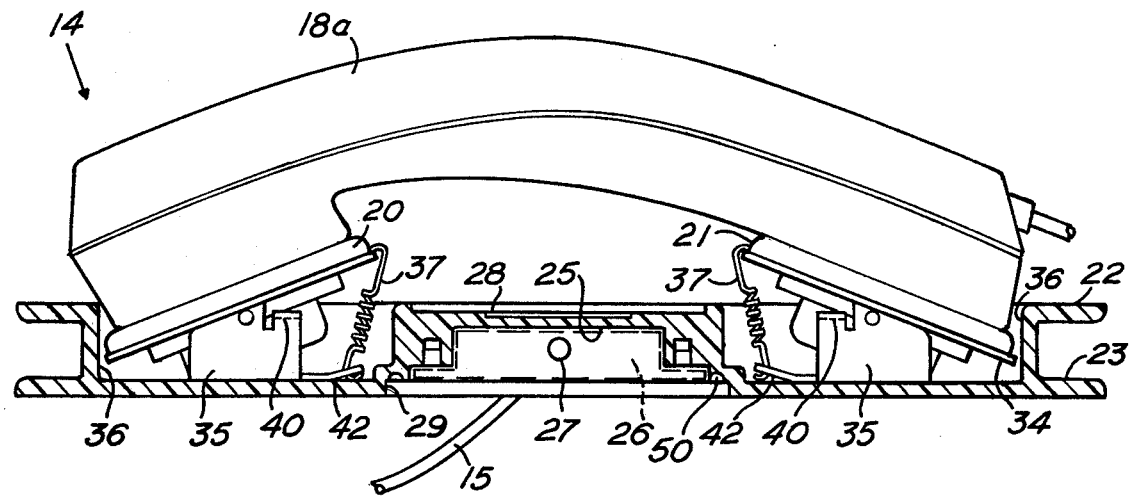

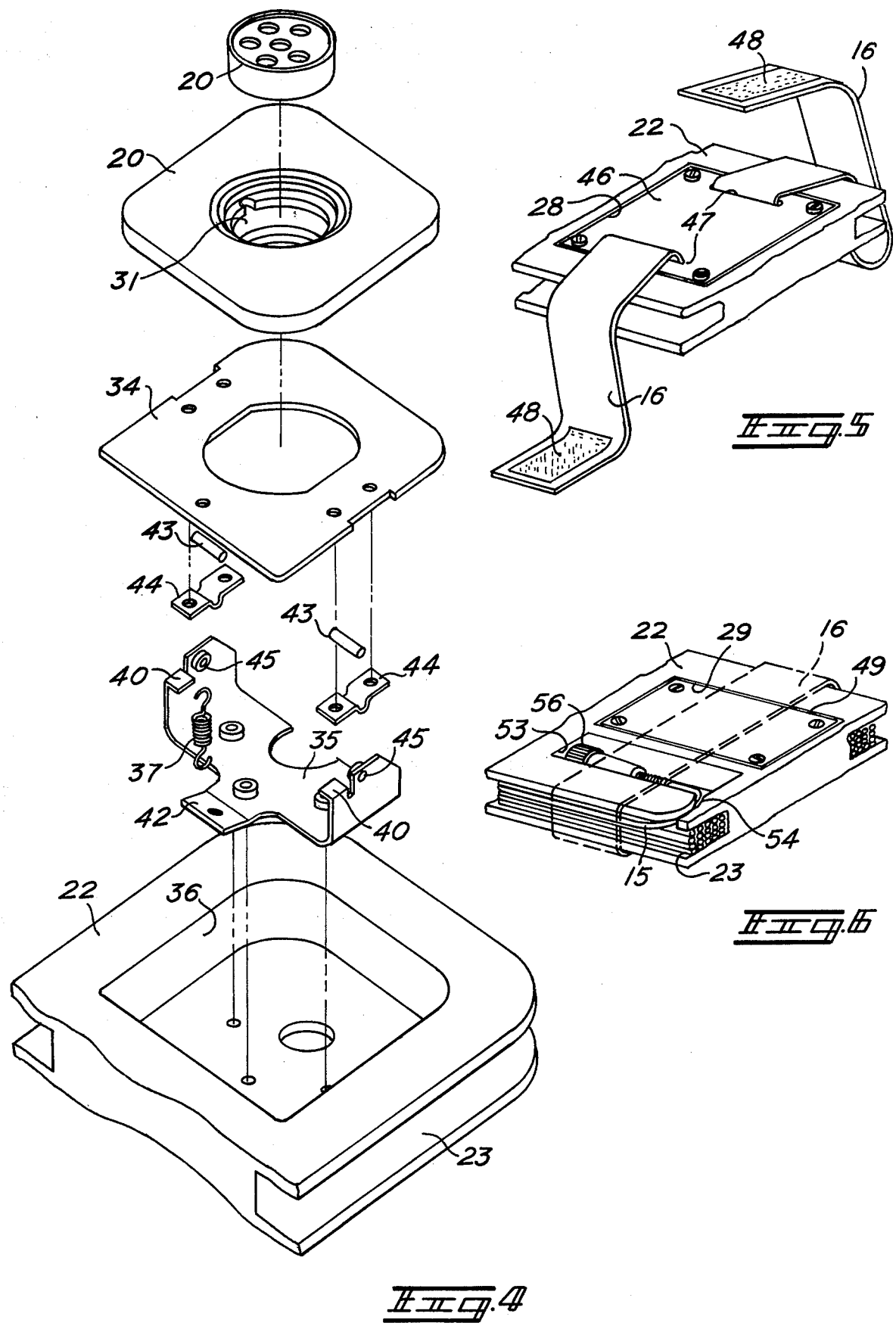

REMOTE TELEPHONE COUPLER AS FOR MEDICAL EMERGENCY DATA TRANSMISSION

BACKGROUND OF THE INVENTION

The present invention relates to the field of telephone couplers and more specifically to portable couplers as for medical data transmission in cooperation with any available telephone handset.

In the field of emergency medicine, it is well known to equip a team of paramedics with patient monitoring devices such as an electrocardiograph, and with a two-way radio for transmitting EKG data to a hospital. Such equipment includes a handset for duplex voice communication with the hospital. Under certain circumstances, however, this system may not function satisfactorily. The scene of the emergency might be beyond radio range, or within normal range but in a location where transmission is difficult or impossible. Also, all available radio channels might be in use at the critical time.

Under any of these circumstances, it would be advantageous to use telephone lines if a telephone and a coupler unit attached to the emergency radio were available. Such a unit would need to be as small as possible, since storage space in an ambulance is at a premium. A long cable would be needed, with a suitable cable holder, since the nearest phone might be on a different floor of a building or away from a roadside. The coupler would also have to be usable with any telephone handset configuration; i.e. having any angular relationship between the ear and mouthpieces. This adaptability is critical since air-tight coupling between handset and transducers is a necessity for accurate data transmission. Acoustic couplers are well known as used with data terminals, but these are designed to provide the necessary type coupling for only one particular handset configuration and would not be usable with, for example, the Trimline™ phone. All previous attempts to provide a portable coupler having all these required characteristics have been unsatisfactory for various reasons.

SUMMARY OF THE INVENTION

It is, therefore, an object of the present invention to provide a portable telephone coupler for data transmission which automatically adapts to any telephone handset configuration.

It is a further object to provide an adaptable unit having an extra long connecting cable and requiring a minimum of storage space.

These objectives and others are provided in a coupler constructed in accordance with the invention and having a very thin, rigid base which is the spool for a lengthy connecting cable. A releasable strap around the spool holds the cable and connector plug in place during storage. Transducers are mounted within depressed areas of the base and, in the released or storage position, are wholly within the base. Each transducer is supported by a resilient coupler pad and each pad is mounted on a pivotably mounted and spring biased plate. As the ear or mouth portion of a telephone handset contacts a resilient pad, the pivoted plate automatically adjusts to the correct angle for tight acoustic coupling. The dual purpose strap which during storage held the cable on the spool then functions to retain the handset tightly against the coupler pads.

BRIEF DESCRIPTION OF THE DRAWING

FIG. 2 is a side view of the coupler unit of FIG. 1 when not in use.

FIGS. 3A and 3B are cut-away views of the coupler unit as self-adjusted to two different telephone handsets.

FIG. 4 is an exploded view of a portion of the coupler unit.

FIG. 5 is a perspective view of the top side of the central portion of the coupler assembly.

FIG. 6 is a perspective view of the bottom side of the central portion of the assembly.

DETAILED DESCRIPTION OF A PREFERRED EMBODIMENT

Figure 1:
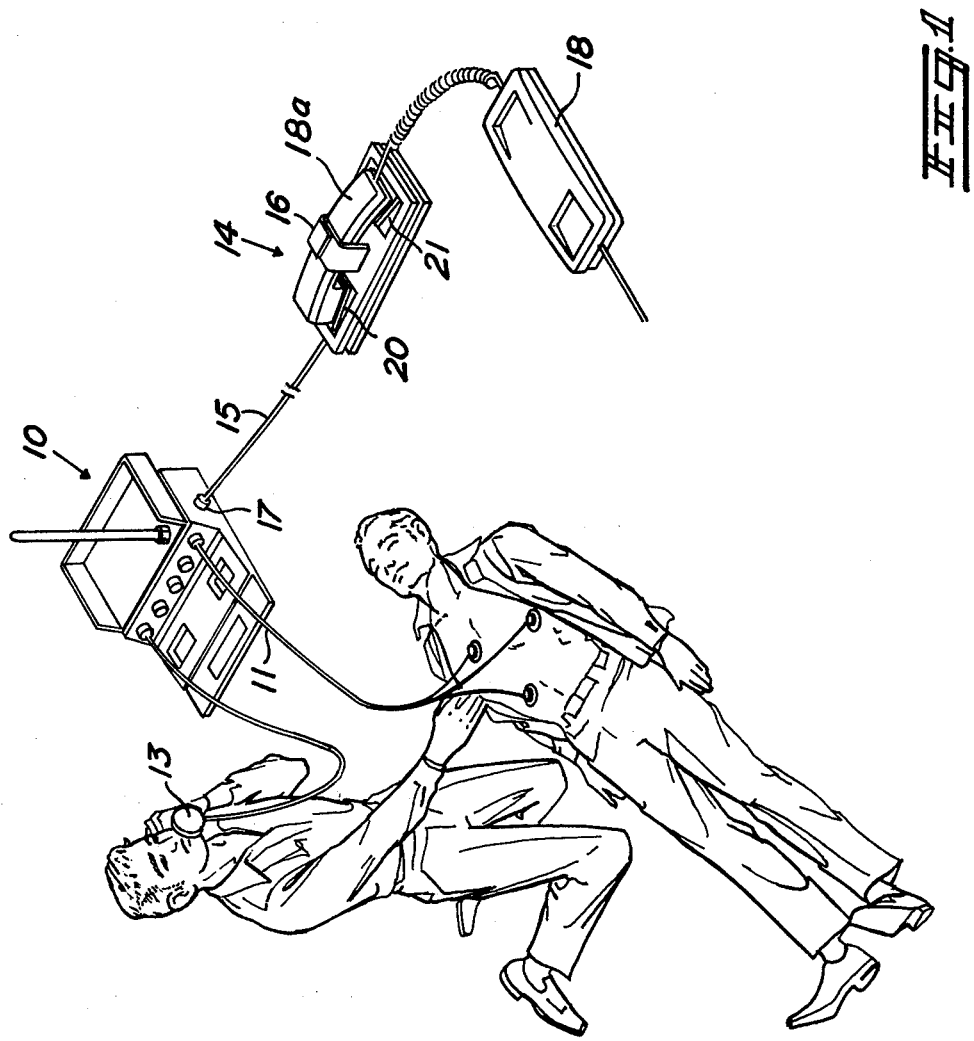
FIG. 1 is a perspective of a system utilizing the invention.

The present invention will be best understood in relation to a system and a situation in which it could be advantageously used. Such a system is illustrated by way of example only in FIG. 1 and would include a medical emergency duplex radio unit 10. The patient will be coupled by a cable 11 to an electrocardiograph modulator in the emergency unit 10 for transmitting the EKG data back to a base station, typically in a hospital. In normal usage, a paramedic might attach the electrodes of the cable 11 to the patient's chest, then contact the hospital by radio, using a handset 13 on the emergency unit 10 as microphone/speaker. The paramedic would be able to give the circumstances of the emergency situation to more highly skilled personnel at the hospital and when the EKG data had been read at the hospital, any necessary instructions could be given to the paramedic. In any case wherein the radio cannot be used; i.e., distance, interference, no usable channel, a coupler assembly 14 of the invention is required.

In these circumstances, a coupler cable 15 is released from a dual purpose retaining strap 16, unwound and plugged into socket 17 on the emergency radio 10. The transmitter is disabled. The coupler unit 14 is then taken to the nearest telephone 18 and a call placed to the hospital. After the connection is made between the telephone 18 and the hospital, the telephone handset 18a is placed against two coupler pads 20, 21 on the coupler assembly 14. The retaining strap 16 is then fastened tightly around the handset 18a and the handset is now acoustically coupled to the coupler pads 20, 21 as will be further described hereinafter. The paramedic can now function exactly as in the normal case of radio transmission; i.e., the EKG data is sent to the hospital, and duplex communication between the hospital and the paramedic at the patient's side is carried on by means of the handset 13 of the emergency radio unit 10.

Typically, the patient would not be moved until his condition was known and the paramedic informed as to the proper treatment to be given, either at the emergency location or en route to the hospital.

FIG. 2 shows a side view of the coupler assembly 14 in storage condition. A base/spool 22 is preferably molded of a strong, rigid insulating material such as a polycarbonate resin. The long coupler cable 15 is wound around the base/spool 22 within a groove 23, and is retained by the strap 16.

In FIGS. 3A and 3B cut-away views of the coupler assembly 14 show its use with two different handsets, the pertinent difference being in the angles between the surfaces of the ear and mouthpieces. This preferred embodiment of the base/spool 22 has a cavity 25 on the bottom side for containing electrical circuitry 26 (position indicated by dashed line). One end of the long connecting cable 15 enters by a small aperture 27 at the bottom of the groove 23. Two shallow recesses 28 and 29 receive top and bottom plates respectively as will be described later. The plates and the strap 16 are omitted here for clarity. Each of two transducers 30 (one visible in FIG. 3A) is retained within a recess 31 in one of the resilient pads 20, 21. The pads 20, 21 are preferably molded of a material such as ethylene propylene and each is mounted on a pivotable plate 32 by means of a slot 33 molded into each pad. While the pads 20, 21 may be a snap-in design as shown, other means of attaching the pad to the plate 34 are also within the scope of the invention.

Each pivotable plate 34 is mounted on a pivot bracket 35 attached to the bottom of a recess 36 in the base/spool 22, and each is normally biased by a spring 37 (one shown in FIG. 3A) into a position flush with the upper surface of the base/spool 22. Upon pressure on the pads by the edges of telephone ear and mouthpieces, the pads 20, 21 and pivotable plates 34 will pivot until each pad is parallel to the plane of the contacting portion of the ear or mouthpiece. As may be seen in FIG. 3B the required pivot angle for some telephone handsets may be greater (sometimes less) than for the more typical one of FIG. 3A. It will be seen that the coupler unit could be constructed with only one plate 32 pivotable.

FIG. 4 shows an exploded view of one section of the coupler assembly 14, including a portion of the base/spool 22 and peripheral groove 23 which, during storage, retains the cable 15. One of the recesses 36 is also shown. The pivot bracket 35 is fastened to the base/spool 22 by screws (not shown) which are inserted through the base/spool and threaded into the bracket 35. A portion 40 of each bracket 35 is formed to provide a stop for the pivotable plate 34 when the plate is released from contact with the telephone handset and the biasing spring 37 pulls the plate 34 back into the recess 36. The spring 37 is attached to an angled portion 42 of the bracket 35 and to the edge of the pivotable plate 34 nearest the center of the coupler unit. On the underside of each pivotable plate 34 two pivot pins 43 are fixedly attached, preferably by two pin brackets 44. The pins 43 are rotatably retained in apertures 45 in the pivot bracket 35.

FIG. 5 shows a portion of the base/spool 22 with a top plate 46 in the recess 28. The dual purpose strap 16 is preferably retained by being inserted through two slots 47 in the top plate 46, but other retaining methods may be employed. The preferred embodiment of the strap is a strong nylon web having at least two Velcro™ sections 48 at or near the ends of the strap for easy fastening and releasing.

In FIG. 6, the bottom view of the base/spool 22 shows a bottom plate 49 in the recess 29, covering the circuitry 26 in the recess 25. The recess 29 includes a groove 50 for receiving a gasket (not shown) for sealing the recess 29. Adjacent the cover plate 52 is a recess 53 with adjoining notch 54 for receiving a connector 56 on the end of the long coupler cable 15. When the coupler cable 15 is wrapped around the base/spool 22 for storage, the connector 56 is placed within the recess 53 before the retaining strap 16 is fastened around the base/spool 22. The position of the strap 16 after fastening is indicated by the dashed line 58.

Other fasteners could, of course, be used on the retaining strap. The dimensions of the strap and the fastener portions are chosen to provide the dual function of alternatively retaining the cable 15 in the groove 23 or holding a telephone handset against the coupler pads 20 and 21. Another cover plate (not shown), having no slots fits into the bottom recess 29 of the base/spool 22 and the circuitry 26 is sealed by a gasket (not shown) in a groove 50 in the recess 29.

Thus, there has been disclosed a portable assembly for acoustically coupling to any of a number of telephone handsets for transmitting data. The necessarily long cable is wound in a peripheral groove in the base/spool of the unit and retained by a dual purpose strap which alternatively retains a telephone handset tightly against the coupler pads which hold the transducers. The transducers are pivotably supported and are retracted into the base/spool when not in use, providing an assembly with minimal space requirements for storage.

What is claimed is:

1. A portable coupler assembly, self-adjustable for use with any of a plurality of telephone handset configurations, comprising in combination:
   a thin base member having at least one cavity in a main surface area, and having a peripheral groove;
   circuit means retained within said cavity in the base member;
   cable means coupled to said circuit means and adapted to be stored within said peripheral groove of the base member;
   resilient coupler means having a substantially flat upper surface, having a central aperture in said flat surface, said coupler being normally positioned within said base cavity and being pivotably mounted for cooperating with any of the handset configurations;
   a retaining means attached to said base and having a first position for releasably retaining said handsets in tight contact with said coupler means and a second position for retaining said cable means within said peripheral groove of the base member; and
   transducer means coupled to said circuit means and retained within said central aperture of the coupler means for providing audio signal coupling with said retained handsets.

2. A remote coupler assembly according to claim 1 wherein the coupler means comprises two spaced apart couplers, mounted to pivot independently in a single plane.

3. A remote coupler assembly according to claim 1 wherein the base member comprises a molded, rigid plastic portion and cover means for covering the circuit means and for attaching the retaining means.

4. A remote coupler assembly according to claim 3 wherein the cover means comprises a first plate member releasably attached to one main surface of the base member for covering the circuit means and a second plate member releasably attached to another main surface of the base member and having two apertures therein for coupling to the retaining means.

5. A remote coupler assembly according to claim 1 wherein the retaining means comprises an elongated flexible web and at least two fastener means positioned near the ends of the web for releasably mating said ends in each of said positions.

6. A remote coupler assembly according to claim 1 and further including a connector means on the second end of the cable means, the connector means being retained within a cavity in the base member.

* * * * *